United States Patent
Keller et al.

(10) Patent No.: US 7,529,576 B2
(45) Date of Patent: May 5, 2009

(54) DEVICE AND METHOD FOR MEASURING BLOOD FLOW IN AN ORGAN

(75) Inventors: Emanuela Keller, Kilchberg (CH); Andreas Nadler, Wädenswil (CH); Peter Niederer, Zürich (CH)

(73) Assignees: Universitat Zürich, Zürich (CH); ETH Zürich, Zürich (CH)

( * ) Notice: Subject to any disclaimer, the term of this patent is extended or adjusted under 35 U.S.C. 154(b) by 613 days.

(21) Appl. No.: 10/816,306

(22) Filed: Apr. 1, 2004

(65) Prior Publication Data

US 2004/0249275 A1 Dec. 9, 2004

(30) Foreign Application Priority Data

Apr. 5, 2003 (DE) ............................ 103 15 574

(51) Int. Cl.
*A61B 6/00* (2006.01)

(52) U.S. Cl. .................. 600/431; 600/473; 600/504; 356/39; 356/51

(58) Field of Classification Search ......... 600/407–480, 600/309, 310, 314, 322–324, 317, 504; 356/39, 356/51, 300, 302, 303
See application file for complete search history.

(56) References Cited

U.S. PATENT DOCUMENTS 4,281,645 A * 8/1981 Jobsis ..................... 600/324
5,527,822 A * 6/1996 Scheiner ................. 514/465
5,999,841 A 12/1999 Aoyagi et al.
6,216,021 B1 * 4/2001 Franceschini et al. ....... 600/310

(Continued)

FOREIGN PATENT DOCUMENTS

EP 0 615 723 9/1994

(Continued)

OTHER PUBLICATIONS

A. Nadler, R. Mudra, E. Keller, H. Alkadhi, P. Niederer. Noninvasive Measurement of Regional Cerebral Blood Flow by Near Infrared Spectroscopy and Indocyaningreen Dye Dilution. <http://149.171.88.70/wc2003$/pdf/2525.pdf> (accessed Dec. 20, 2006).*

(Continued)

*Primary Examiner*—Ruth S Smith
*Assistant Examiner*—Amanda L. Lauritzen
(74) *Attorney, Agent, or Firm*—Collard & Roe, P.C.

(57) ABSTRACT

A device has a source for emitting near infrared radiation into cerebral tissue, a sensor for detecting radiation exiting from the tissue, and an evaluation unit which detects the exiting radiation as an input signal having pulsatile and non-pulsatile components and is programmed to determine the concentration of an injected indicator in the tissue from the non-pulsatile signal component, iteratively determine an inflow function characterizing cerebral blood flow by varying a mean transit time until reaching a stop criterion, determine indicator concentration relative to cerebral blood volume from the inflow function and the pulsatile signal component, calculate cerebral blood volume by dividing indicator concentration in the tissue by indicator concentration relative to cerebral blood volume, calculate cerebral blood flow by dividing the cerebral blood volume by the mean transit time when the stop criterion has been reached, and scale the inflow function using values determined from the pulsatile signal component.

22 Claims, 2 Drawing Sheets

U.S. PATENT DOCUMENTS

| | | | |
|---|---|---|---|
| 6,223,069 B1 | 4/2001 | Pfeiffer et al. | |
| 6,246,901 B1* | 6/2001 | Benaron | 600/431 |
| 6,339,714 B1 | 1/2002 | Chen | |
| 6,516,214 B1* | 2/2003 | Boas | 600/431 |
| 6,606,509 B2* | 8/2003 | Schmitt | 600/310 |
| 6,709,402 B2* | 3/2004 | Dekker | 600/529 |
| 6,802,812 B1* | 10/2004 | Walker et al. | 600/309 |
| 7,024,234 B2* | 4/2006 | Margulies et al. | 600/324 |
| 7,047,055 B2* | 5/2006 | Boas et al. | 600/338 |
| 7,120,481 B2* | 10/2006 | Keller et al. | 600/339 |
| 7,191,110 B1* | 3/2007 | Charbel et al. | 703/11 |
| 2002/0183621 A1 | 12/2002 | Pfeiffer et al. | |
| 2007/0148260 A1* | 6/2007 | Denault | 424/608 |

FOREIGN PATENT DOCUMENTS

| | | |
|---|---|---|
| EP | 0 374 190 | 1/1997 |
| EP | 0 928 156 | 8/1997 |
| EP | 0 616 791 | 7/1999 |
| WO | WO98/08434 | 3/1998 |

OTHER PUBLICATIONS

E. Keller, M. Wolf, M. Martin, Y. Yonekawa. Estimation of Cerebral Oxygenation and Hemodynamics in Cerebral Vasospasm Using Indocyaningreen Dye Dilution and Near Infrared Spectroscopy: A Case Report. Jan. 2001. Jrnl of Neurosurgical Anesthesiology: vol. 13(1), pp. 43-48.*

Obrist W. D. et al. Regional Cerebral Blood Flow Estimated by 133-Xenon Inhalation. Stroke 6: 245-256 (1975).*

European Search Report, dated Jul. 21, 2004.

Keller E. et al: "New Methods for Monitoring Cerebral Oxygenation and Hemodynamics in Patients with Subachnoid Hemorrhage" ACTA Neurochirurgica. Supplement., Bd. 82, 2002, Seiten 87-92, XP008033028 Austria.

Hoeft A. et al.: "Bedside Assessment of Intravascular Volume Status in Patients Undergoing Coronary Bypass Surgery" Anesthesiology, Bd. 81, Nr. 1, 1994, Sieten, 76-86, XP008033021 Hagerstown.

* cited by examiner

DEVICE AND METHOD FOR MEASURING BLOOD FLOW IN AN ORGAN

CROSS REFERENCE TO RELATED APPLICATIONS

Applicants claim priority under 35 U.S.C. §119 of German Application No. 103 15 574.0 filed Apr. 5, 2003.

BACKGROUND OF THE INVENTION

1. Field of the Invention

The present invention relates to a device for measuring the blood flow in an organ, using an injected indicator.

2. The Prior Art

Devices for measuring the blood flow in an organ, particularly the cerebral blood flow (CBF), using an injected, essentially inert indicator, have been known for a long time, and some of them are in clinical use. Devices based on older methods, such as the xenon dilution technique (Obrist, W. D., Thompson, H. K., Wang, H. S., and Wilkinson, W. F. 1975, *Regional cerebral blood flow estimated by* 133 *xenon inhalation. Stroke* 6: 245-256), are often difficult to implement, in technical terms, and prove to be time-consuming to use. Recently, technologies that use near-infrared spectroscopy (NIRS) in combination with indocyaningreen (ICG) as an indicator, in order to investigate or monitor cerebral blood flow, have gained in importance.

Generally, the use of such devices requires the invasive measurement of the input function, i.e. the arterial concentration of the indicator over time. In this connection, arterial fiber optic catheters are used, for example.

Most recently, the use of non-invasive measurement methods for monitoring cerebral blood flow have also been proposed (Keller, E., Wolf, M., Martin, M., Fandino, J. and Yonekawa, Y. 2001. *Estimation of cerebral oxygenation and hemodynamics in cerebral vasospasm using indocyaningreen (ICG) dye dilution and near infrared spectroscopy (NIRS). A case report. J. Neurosurg. Anesthesiol.* 13: 43-48). In this connection, optodes are affixed to the head, which function as transmitters and receivers of the near infrared radiation, by means of which the indicator concentration in the cerebral vascular system is determined. The algorithms used for evaluation are described in the literature (Keller, E., Nadler, A., Imhot, H.-G., Niederer, P., Roth, P. and Yonekawa, Y. 2002. *New Methods of Monitoring Cerebral Oxygenation and Hemodynamics in Patients with Subarachnoid Hemorrhage. Acta Neurochir. [Suppl.]* 82: 87-92).

A significant problem of conventional NIRS devices is that their evaluation units work with a certain inaccuracy, which arises because in the evaluation, until now, the point of departure has been the simplifying assumption that no flow of the indicator out of the system being investigated takes place during the first rise in the input signals (the so-called "rise time"). The accuracy of the results delivered within the scope of the evaluation therefore decisively depends on the sharpness of the first peak of the measurement signal after administration of the indicator. Since injection of the indicator cannot be performed in a time that is as short as desired, and at a location that is as close to the measurement location as desired, for obvious practical reasons, the dependence of the quality of the measurement results on the sharpness of the first peak of the measurement signal after administration of the indicator was accepted as being fundamental, until now.

Alternative measurement methods, such as positron emission tomography (PET), single-photo photon emission computer tomography (SPECT), or perfusion-weighted magnetic resonance spectroscopy can be implemented technically only by means of extremely expensive devices, and require transport of the patient in question to the measurement unit, in order to be used, and this transport often poses significant risk to the patient; in other words, the devices mentioned cannot be used as so-called "bedside" devices at the patient's bed.

SUMMARY OF THE INVENTION

It is an object of the present invention to provide a device that can achieve greater accuracy in the determination of the blood flow in an organ, particularly the cerebral blood flow. In particular, the accuracy of the evaluation results should be less dependent on the general conditions, i.e. particularly on how the indicator injection was performed. Furthermore, the device should be non-invasive, and also implementable with a reasonable technical effort/expenditure.

According to one aspect of the present invention, this object is achieved with a device for measuring the blood flow in an organ, using an injected indicator which includes a radiation source for emitting near infrared radiation into tissue of te organ at a first location, a sensor for detecting a proportion of the emitted near infrared radiation that exits from the organ at a second location, and an evaluation unit that detects the proportion of emitted near infrared radiation that exits from the tissue of the organ as an input signal. The input signal is composed of a pulsatile component and a non-pulsatile component. The evaluation unit is set up, in terms of program technology, to perform the following steps:

(a) determination of the concentration of injected indicator, with reference to the tissue of the organ, from the non-pulsatile component of the input signal, (b) iterative determination of an inflow function i(t) that characterizes the blood flow through the organ, by variation of a mean transit time mtt until a stop criterion is reached, (c) determination of the concentration of injected indicator, with reference to the blood volume in the organ, from the pulsatile component of the input signal and the iteratively determined inflow function i(t), (d) calculation of the blood volume in the organ as a quotient of the concentration of injected indicator with reference to the tissue of the organ and the concentration of injected indicator with reference to the blood volume in the organ, and (e) calculation of the blood flow in the organ as a quotient of the blood volume in the organ and the mean transit time mtt when the stop criterion has been reached.

Advantageous embodiments of the device according to the invention are described below.

One of the advantages of the present invention is that the sharpness of the first peak of the measurement signal after administration of the indicator is no longer decisive for the accuracy of the results achieved, something that is completely surprising to a person skilled in the art, since the evaluation unit also takes the flow of indicator out of the organ during the first rise in the input signal into consideration, because of its program technology set-up according to the invention.

BRIEF DESCRIPTION OF THE DRAWINGS

Other objects and features of the present invention will become apparent from the following detailed description considered in connection with the accompanying drawings. It should be understood, however, that the drawings are designed for the purpose of illustration only and not as a definition of the limits of the invention.

In the drawings.

DETAILED DESCRIPTION OF PREFERRED EMBODIMENTS

Figure 1:
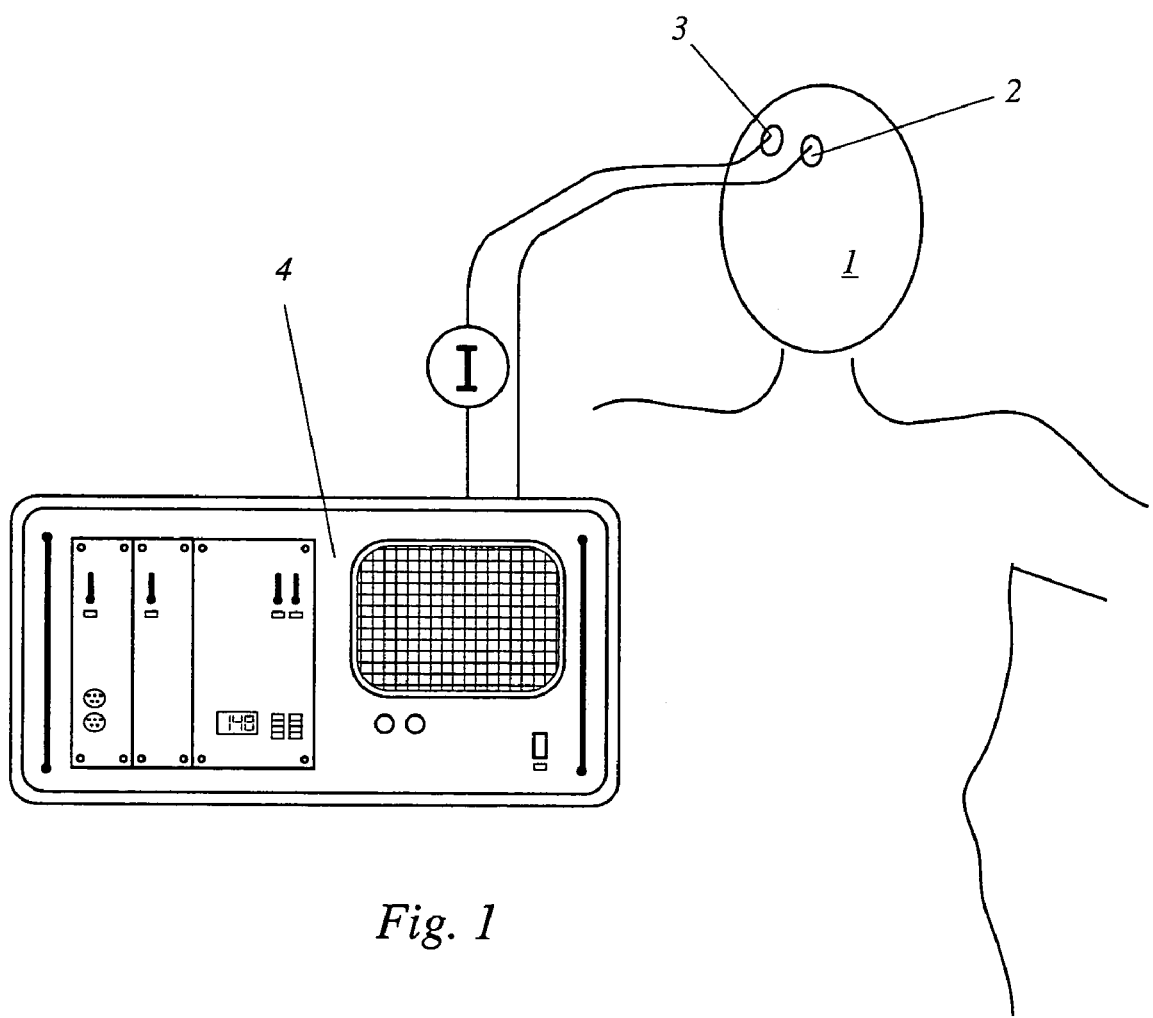
FIG. 1 shows schematically, the most important components of an embodiment for determining the cerebral blood flow of a patient, in accordance with the invention.

The device according to the invention shown schematically in FIG. 1 serves to determine the cerebral blood flow of a patient, for example an intensive-care patient in neurosurgery. A first optode 2 and a second optode 3 are attached to the head 1 of the patient, by means of an elastic band (not shown), at an optimized distance from one another. A radiation source (not shown) for emitting near infrared radiation into the cerebral tissue of the patient is arranged either in first optode 2 itself, or separately from it, for example in a common housing with the evaluation unit 4. Where the radiation source is separate from first optode 2, the near infrared radiation is passed by means of a light guide to first optode 2, where the radiation is emitted. The wavelength of the emitted radiation and the indicator used must be coordinated with one another. For the indicator usually used, indocyaningreen, a wavelength of about 805 nm (but definitely in the range between 780 and 910 nm) is ideal. The intensity of the proportion of the infrared radiation that exits from the cerebral tissue at the location of second optode 3 is detected by second optode 3 and passed to the evaluation unit 4.

This proportion of radiation is higher or lower, depending on the concentration of the indicator injected into the cerebral tissue of the patient. The indicator concentration with reference to the cerebral tissue depends on the indicator concentration in the blood that flows through the tissue, as well as on the amount of the blood that flows through the tissue. The amount of blood that flows through the tissue changes periodically, with the heartbeat, and for this reason the intensity signal received has a pulsatile component, i.e. a periodically varying component. The pulsatile component of the intensity signal has a non-pulsatile component superimposed on it.

The indicator concentration in the blood that flows through the tissue changes over time, because the blood that flows out of the cerebral tissue has a different concentration from the blood that is flowing in. The distribution kinetics of the indicator in the cerebral vascular system are partly responsible for this difference in concentration. The indicator concentration in the recirculated blood (blood newly flowing in) is determined by the distribution kinetics of the indicator in the entire circulatory system and by the decomposition of the indicator in the liver.

Evaluation unit 4 is set up, in terms of program technology, for performing the evaluation steps listed in FIG. 2 in the form of a flow chart, which will be explained below.

The optical density OD is formed from the intensity signal as a negative decadic logarithm of the transmission. In this connection, transmission is understood to be the quotient of the intensity of the detected near infrared radiation and the intensity of the emitted near infrared radiation (and not in the strictly physical sense, since the detected radiation includes scattered and reflected components).

The (time-dependent) optical density, which is essentially proportional to the indicator concentration in the tissue, is divided up into its pulsatile component and its non-pulsatile component.

An inflow function $i(t)$ that corresponds to the arterial input function of the brain is iteratively determined from the non-pulsatile component. The sequence of the iteration is shown in the left branch of the schematic shown in FIG. 2. A suitable mean transit time mtt, for example mtt=7 s, is chosen as a starting parameter. The mean transit time mtt is sometimes also referred to as the "pass-through" time, and is a characteristic dwell time that corresponds to the time that a volume element needs, on the average, in order to pass through the system being considered.

In an initialization step, the time variable t, as well as the inflow function $i(t)$ for the range t<0, and the related outflow function $o(t)$, are set to zero.

The inflow function $i(t)$ describes the proportion of the change in the concentration of the indicator in the cerebral tissue that comes from the amount of inflowing blood; the outflow function $o(t)$ describes the proportion of the change in the concentration of the indicator in the cerebral tissue that comes from the amount of outflowing blood. The time immediately after the injection of indicator is t=0.

Each iteration step includes a step-by-step calculation of an approximation of the inflow function $i(t)$ and an approximation of the outflow function $o(t)$, as well as the calculation of an approximation of the transport function $g(t)$, so that the $m^{th}$ approximation of the inflow function $i(t)$, the outflow function $o(t)$, and the transport function $g(t)$ is calculated with the $m^{th}$ iteration step (let m be the counting variable). In a computing step, the value of the inflow function for the time t is calculated according to the balance equation $$i(t)=d/dt(C_{tissue}(t))+o(t-t_k)$$

In this equation, $t_k$ is a constant small time interval, so that the value of the outflow function at the time $t-t_k$ is to be inserted for $o(t-t_k)$. The term $d/dt\,(C_{tissue}(t))$ expresses the change in the indicator concentration with reference to the cerebral tissue.

Within the framework of the iterative calculation of the inflow function, only relative function values are required, at first, because of scaling that takes place later by means of absolute values of the pulsatile signal component. For this reason, the optical density $OD(t)$ is used for the concentration $C_{tissue}(t)$. Furthermore, the term $d/dt\,(C_{tissue}(t))$ is linearized, so that the above calculation step is implemented in the form $$i(t)=OD(t)-OD(t-t_k)+o(t-t_k).$$

In the next step, the convolution integral $o(t)=i(t)*g(t)$ with the transport function $g(t)$ is used for calculating the value of the outflow function at the time t. The transport function is formed according to one of the usual equations, for example the one published in Hoeft, A., Schom, B., Weyland, A., Scholz, M., Buhre, W., Stepanek, E., Allen, S. J., and Sonntag, H. 1991. *Bedside assessment of intravascular volume status in patients undergoing coronary bypass surgery.* Anesthesiology 81: 76-86, and depends on the mean transit time mtt. A suitable equation is $$g(t)=\frac{1}{\sqrt{2\cdot\pi\cdot\sigma\cdot t}}\cdot e^{-\frac{\left(\ln\frac{t}{mtt}+\frac{\sigma^2}{2}\right)}{2\sigma^2}}$$

In this equation, $\alpha$ is a constant parameter selected for the system on the basis of empirical values (which fundamentally describes the width of an assumed dwell time distribution).

In a next step, the time variable t is increased by the increment $t_k$. If t is smaller than an end value $t_2$, the loop is run through again, starting with the calculation step $$i(t)=OD(t)-OD(t-t_k)+o(t-t_k).$$

If, on the other hand, the end value has exceeded $t_2$, a check is performed in the next step to see whether the function progressions of the inflow function i(t) and the outflow function o(t) are plausible. A plausibility criterion (i.e. a stop criterion of the iteration) may be that neither the inflow function i(t) nor the outflow function o(t) have values below a threshold value. It is suitable to select this threshold value to be greater than or equal to 0. Furthermore, the plausibility criterion can include the requirement that the inflow function i(t) can be represented as the sum of a finite number of functions that are similar to the form of the transport function g(t).

If the function progressions of the inflow function i(t) and the outflow function o(t) are not plausible, the mean transit time mtt is adapted by an increment by means of a suitable increase or decrease, and another iteration step is performed, which again begins with the initialization step and proceeds as explained.

If, on the other hand, the function progressions of the inflow function i(t) and the outflow function o(t) are plausible, the iteration is stopped. The method then continues with the function progression of i(t) that was received and the value of the mean transit time mtt that was received, as described below.

Figure 2:
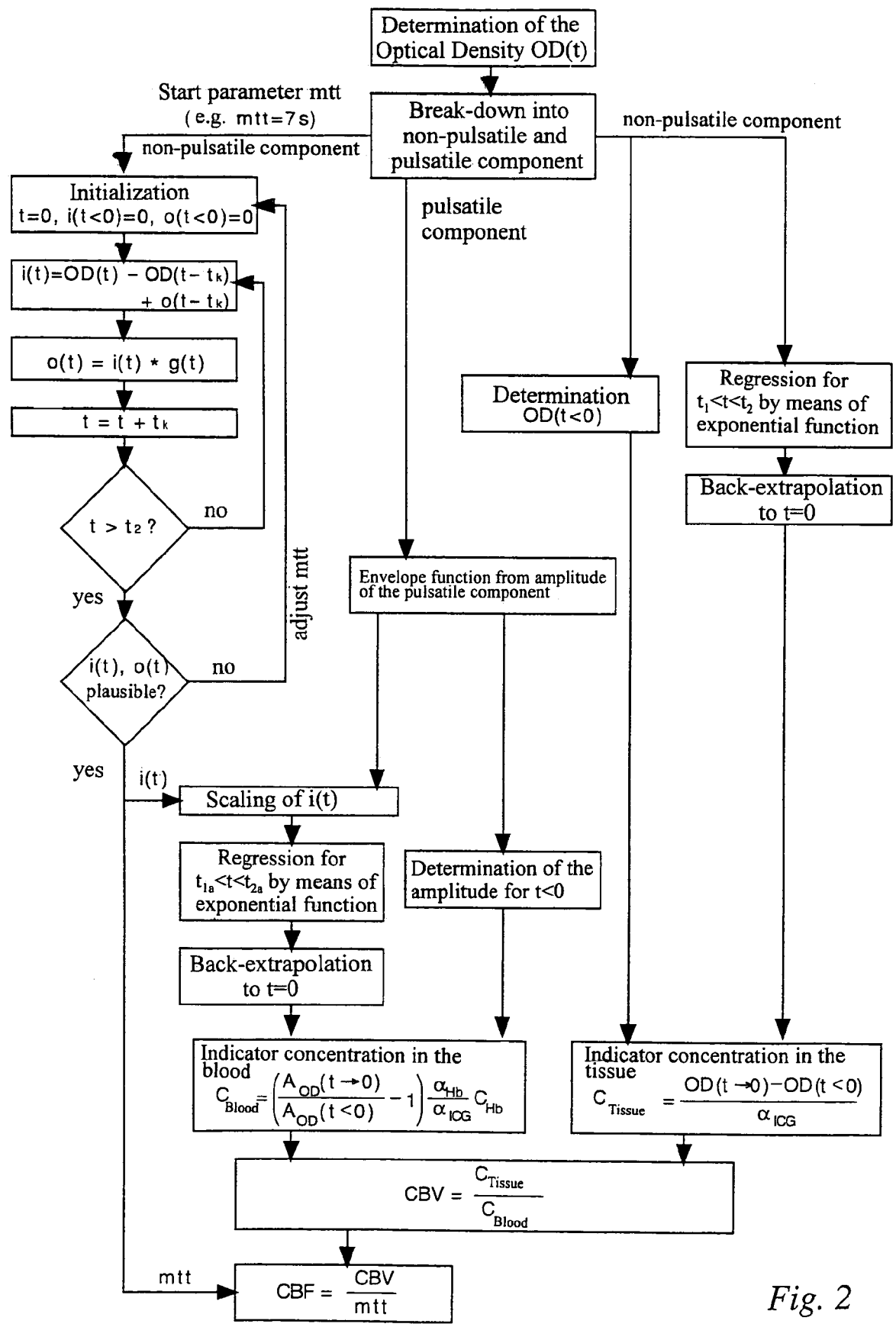
FIG. 2 shows a flow chart of the sequence for the determination of the cerebral blood flow from the input signal, implemented in the evaluation unit in terms of program technology.

The indicator concentration in the tissue is also determined from the non-pulsatile component of the time progression of the optical density OD, as shown in the right branch of the schematic shown in FIG. 2. For this purpose, the non-pulsatile component of the time progression of the optical density OD is simulated in an interval $t_1>0$ to $t_2$, by regression by means of an exponential function, and the density is extrapolated back to the time t=0. The time $t_2$ is selected so that complete mixing of the indicator with the blood is guaranteed, i.e. so that concentration peaks due to recirculation can no longer be determined. Furthermore, the value of the non-pulsatile component is determined in the range t<0, i.e. OD(t<0).

In a next step, the actual calculation of the indicator concentration immediately after injection of the indicator, with reference to the tissue, $C_{tissue}$, takes place, according to the formula $$C_{tissue}=[OD(t \to 0)-OD(t<0)]/\alpha ICG$$

whereby αICG is the absorption coefficient of the indicator, and OD(t→0) corresponds to the value of the optical density OD from the function progression for t approaching 0 that has been extrapolated back.

Evaluation steps implemented in order to take into consideration the pulsatile component are listed in the center branch of FIG. 2. An envelope is adapted to the pulsatile component of the time progression of the optical density OD. Furthermore, the amplitude $A_{OD}(t<0)$, in other words the amplitude of the pulsatile component of the optical density, is determined for t<0.

With the absolute values obtained from the pulsatile signal component, from a range in which the amplitude is great and therefore less susceptible to noise (for example for t from 0 to 60 s), the inflow function i(t) that has previously been determined by iteration is scaled, for example by minimizing the sum of the difference squares $[i(t)-A_{OD}(t)]^2$. In the final analysis, this scaling results in greater accuracy, because while values obtained from direct measurement for greater t values are increasingly distorted by noise, due to lower indicator concentrations, i(t) describes the decrease in the indicator concentration in the blood well, even for great t values.

Proceeding from a time interval of $t_{1a}>0$ to $t_{2a}$, in which the indicator has already been distributed well in the system (i.e. at sufficiently great $t_{1a}$ and $t_{2a}$), the scaled inflow function i(t) is extrapolated back to the time point t=0 (for example by means of an exponential function simulated by means of regression, in the time interval $t_{1a}>0$ to $t_2$).

The indicator concentration in the blood, $C_{blood}$, required for calculating the cerebral blood volume CBV is calculated according to the following formula, wherein $A_{OD}(t>0)$ corresponds to the value of the amplitude of the optical density for t approaching 0 that was obtained from the function extrapolated back (which is less dependent on the sharpness of the first signal peak after administration of the indicator, as compared with a value determined by direct measurement):

$$C_{Blood} = \left(\frac{A_{OD}(t \to 0)}{A_{OD}(t<0)} - 1\right)\frac{\alpha_{Hb}C_{Hb}}{\alpha_{ICG}}.$$

In this equation, αICG is the absorption coefficient of the indicator, $\alpha_{Hb}$ is the absorption coefficient of the hemoglobin, and $C_{Hb}$ is the hemoglobin concentration in the blood.

The cerebral blood volume CBV is calculated as the quotient of an indicator concentration in the blood, $C_{blood}$, and the indicator concentration with reference to the cerebral tissue, $C_{tissue}$, i.e.

$$CBV=C_{tissue}/C_{blood}.$$

The cerebral blood flow CBF is determined as a quotient of the cerebral blood volume CBV and the mean transit time mtt, in other words according to the formula $$CBF=CBV/mtt.$$

Accordingly, while at least one embodiment of the present invention have been shown and described, it is to be understood that many changes and modifications may be made thereunto without departing from the spirit and scope of the invention as defined in the appended claims.

What is claimed is:

1. A device for measuring blood flow in an organ using an injected indicator comprising:
    a radiation source for emitting near infrared radiation into tissue of the organ at a first location;
    a sensor for detecting a proportion of the emitted near infrared radiation that exits from the organ at a second location; and
    an evaluation unit that detects the proportion of the emitted near infrared radiation that exits from tissue of the organ as a single input signal, said evaluation unit being programmed to perform the following evaluation steps:
    (a) dividing up said single input signal into a pulsatile component and a non-pulsatile component;
    (b) determining an injected indicator concentration with reference to the organ tissue from said non-pulsatile component of said single input signal;
    (c) iteratively determining, from said non-pulsatile component, an inflow function i(t) that characterizes blood flow through the organ by incrementally varying a mean transit time mtt until a stop criterion is reached;
    (d) determining an injected indicator concentration with reference to blood volume in the organ from said pulsatile component of said single input signal and the iteratively determined inflow function i(t);
    (e) calculating a blood volume in the organ as a quotient of the injected indicator concentration with reference to the organ tissue and the injected indicator concentration with reference to the blood volume in the organ; and (f) calculating a blood flow in the organ as a quotient of the blood volume in the organ and the mean transit time mtt when the stop criterion has been reached.

2. The device according to claim 1, wherein each iteration step in iteratively determining the inflow function i(t) comprises a step-by-step calculation by approximation of the inflow function i(t) according to the equation $$i(t)=d/dt(C_{tissue}(t))+o(t-t_k)$$

and an outflow function o(t) by means of a convolution integral $$o(t)=i(t)*g(t)$$

wherein $d/dt\,(C_{tissue}(t))$ is a term that describes a change in the injected indicator concentration with reference to the organ tissue, a value of the outflow function o(t) at a time $t-t_k$ is to be inserted for $o(t-t_k)$, and g(t) is a characteristic transport function in which the mean transit time mtt is included.

3. The device according to claim 2, wherein the stop criterion for iteratively determining the inflow function i(t) includes that the inflow function i(t) can be represented as a sum of a finite number of functions that are similar in form to the transport function g(t).

4. The device according to claim 1, wherein the stop criterion for iteratively determining the inflow function i(t) includes that a minimum of the inflow function i(t), determined by means of iteration, is greater than a threshold value.

5. The device according to claim 4, wherein the threshold value is 0.

6. The device according to claim 1, further comprising a non-invasive measurer of blood flow in the organ including means for radiating near infrared radiation in through a patient's skin at the first location and means for capturing the exiting proportion of the emitted near infrared radiation through the patient's skin at the second location.

7. The device according to claim 6, further comprising means for a local reduction of skin perfusion at the first location and the second location by means of applying a locally increased contact pressure.

8. The device according to claim 1, wherein the evaluation unit is programmed to take into consideration that the organ is a patient's brain, the blood flow is cerebral blood flow CBF, and the blood volume is cerebral blood volume CBV.

9. A device for measuring blood flow in an organ using an injected indicator comprising:
  a radiation source for emitting near infrared radiation into tissue of the organ at a first location;
  a sensor for detecting a proportion of the emitted near infrared radiation that exits from the organ at a second location; and
  an evaluation unit that detects the proportion of the emitted near infrared radiation that exits from tissue of the organ as a single input signal, said evaluation unit being programmed to perform the following evaluation steps:
  (a) dividing up said single input signal into a pulsatile component and a non-pulsatile component;
  (b) determining an injected indicator concentration with reference to the organ tissue from said non-pulsatile component of said single input signal;
  (c) iteratively determining, from said non-pulsatile component, an inflow function i(t) that characterizes blood flow through the organ by incrementally varying a mean transit time mtt until a stop criterion is reached;
  (d) determining an injected indicator concentration with reference to blood volume in the organ from said pulsatile component of said single input signal and the iteratively determined inflow function i(t);
  (e) calculating a blood volume in the organ as a quotient of the injected indicator concentration with reference to the organ tissue and the injected indicator concentration with reference to the blood volume in the organ;
  (f) calculating blood flow in the organ as a quotient of the blood volume in the organ and the mean transit time mtt when the stop criterion has been reached; and
  (g) scaling the inflow function i(t) by means of values determined from said pulsatile component of said single input signal.

10. A method for measuring blood flow in an organ of a patient comprising the steps of:
  injecting the patient with an indicator;
  emitting near infrared radiation into tissue of the organ at a first location;
  detecting a proportion of the emitted near infrared radiation that exits from the organ at a second location as a single input signal;
  dividing up said single input signal into a pulsatile component and a non-pulsatile component;
  determining an injected indicator concentration with reference to the organ tissue from said non-pulsatile component of said single input signal;
  iteratively determining, from said non-pulsatile component, an inflow function i(t) that characterizes blood flow through the organ by incrementally varying a mean transit time mtt until a stop criterion is reached;
  determining an injected indicator concentration with reference to blood volume in the organ from said pulsatile component of said single input signal and the iteratively determined inflow function i(t);
  calculating a blood volume in the organ as a quotient of the injected indicator concentration with reference to the organ tissue and the injected indicator concentration with reference to the blood volume in the organ; and
  calculating a blood flow in the organ as a quotient of the blood volume in the organ and the mean transit time mtt when the stop criterion has been reached.

11. The method according to claim 10, wherein each iteration step in iteratively determining the inflow function i(t) comprises a step-by-step calculation by approximation of the inflow function i(t) according to the equation $$i(t)=d/dt(C_{tissue}(t))+o(t-t_k)$$

and of an outflow function o(t) by means of a convolution integral $$o(t)=i(t)*g(t)$$

wherein $d/dt\,(C_{tissue}(t))$ is a term that describes a change in the injected indicator concentration with reference to the organ tissue, a value of the outflow function o(t) at a time $t-t_k$ is to be inserted for $o(t-t_k)$, and g(t) is a characteristic transport function in which the mean transit time mtt is included.

12. The method according to claim 11, wherein the stop criterion for iteratively determining the inflow function i(t) includes that the inflow function i(t) can be represented as a sum of a finite number of functions that are similar in form to the transport function g(t).

13. The method according to claim 10, wherein the stop criterion for iteratively determining the inflow function i(t) includes that a minimum of the inflow function i(t) determined by means of iteration is greater than a threshold value.

14. The method according to claim 13, wherein the threshold value is 0.

15. The method according to claim 10, wherein the indicator has an absorption coefficient that decreases with an increasing indicator concentration and the absorption coefficient is used for determining the injected indicator concentration with reference to the blood volume in the organ.

16. The method according to claim 10, wherein a skin perfusion is reduced at the first location and the second location by means of applying a locally increased contact pressure.

17. The method according to claim 10, wherein the organ is a the brain, the blood flow is cerebral blood flow CBF, and the blood volume is cerebral blood volume CBV.

18. The method according to claim 10, wherein the indicator is indocyaningreen.

19. A method for measuring blood flow in an organ comprising the steps of:
- injecting an indicator;
- emitting near infrared radiation, into tissue of the organ at a first location;
- detecting a proportion of the emitted near infrared radiation that exits from the organ at a second location as a single input signal;
- dividing up said single input signal into a pulsatile component and a non-pulsatile component;
- determining an injected indicator concentration with reference to the organ tissue from said non-pulsatile component of said single input signal;
- iteratively determining, from said non-pulsatile component, an inflow function i(t) that characterizes blood flow through the organ by incrementally varying a mean transit time mtt until a stop criterion is reached;
- determining an injected indicator concentration with reference to blood volume in the organ from said pulsatile component of said single input signal and the iteratively determined inflow function i(t);
- calculating a blood volume in the organ as a quotient of the injected indicator concentration with reference to the organ tissue and the injected indicator concentration with reference to the blood volume in the organ;
- calculating a blood flow in the organ as a quotient of the blood volume in the organ and the mean transit time mtt when the stop criterion has been reached; and
- scaling the inflow function i(t) by means of values determined from said pulsatile component of said single input signal.

20. The method according to claim 19, wherein the step of determining the concentration of injected indicator with reference to the blood volume in the organ comprises back-extrapolating the scaled inflow function i(t) to a time of injection of the indicator.

21. A method according to claim 19, wherein the indicator is indocyaningreen.

22. A device for measuring blood flow in an organ using an injected indicator comprising:
- a radiation source for emitting near infrared radiation into tissue of the organ at a first location;
- a sensor for detecting a proportion of the emitted near infrared radiation that exits from the organ at a second location; and
- an evaluation unit that detects the proportion of the emitted near infrared radiation that exits from tissue of the organ as a single input signal, said evaluation unit being programmed to perform the following evaluation steps:
  - (a) dividing up said single input signal into a pulsatile and a non-pulsatile component;
  - (b) determining an injected indicator concentration with reference to the organ tissue from said non-pulsatile component of said single input signal;
  - (c) iteratively determining, from said non-pulsatile component, an inflow function i(t) that characterizes blood flow through the organ by incrementally varying a mean transit time mtt until a stop criterion is reached;
  - (d) determining an injected indicator concentration with reference to blood volume in the organ from said pulsatile component of said single input signal and the iteratively determined inflow function i(t);
  - (e) scaling the inflow function i(t) by means of values determined from said pulsatile component of said single input signal;
  - (f) back-extrapolating the scaled inflow function i(t) to a time of injection of the indicator;
  - (g) calculating a blood volume in the organ as a quotient of the injected indicator concentration with reference to the organ tissue and the injected indicator concentration with reference to the blood volume in the organ; and
  - (h) calculating a blood flow in the organ as a quotient of the blood volume in the organ and the mean transit time mtt when the stop criterion has been reached.

* * * * *